(12) United States Patent
Singla et al.

(10) Patent No.: US 8,114,895 B2
(45) Date of Patent: Feb. 14, 2012

(54) USE OF BIPYRIDINE COMPOUND 'CAERULOMYCIN A' DERIVATIVES AND ANALOGS THEREOF AS IMMUNOSUPPRESSIVE AGENTS

(75) Inventors: Arvind Kumar Singla, Chandigarh (IN); Javed Naim Agrewala, Chandigarh (IN); Rakesh Mulraj Vohra, Chandigarh (IN); Ravinder Singh Jolly, Chandigarh (IN)

(73) Assignee: Council of Science and Industrial Research, New Delhi (IN)

( * ) Notice: Subject to any disclaimer, the term of this patent is extended or adjusted under 35 U.S.C. 154(b) by 1526 days.

(21) Appl. No.: 11/519,200

(22) Filed: Sep. 12, 2006

(65) Prior Publication Data

US 2007/0078167 A1    Apr. 5, 2007

(30) Foreign Application Priority Data

Sep. 12, 2005    (IN) .......................... 2465/DEL/2005

(51) Int. Cl.
*A61K 31/44*    (2006.01)
(52) U.S. Cl. ....................................... 514/334; 514/332
(58) Field of Classification Search ........................ None
See application file for complete search history.

(56) References Cited

OTHER PUBLICATIONS

Chatterjee et al., "Caerulomycin, an antifungal antibiotic with marked in vitro and in vivo activity against *Entamoeba histolytica*," Z Parasitenkd, 1984; 70(5): pp. 569-573.*
Agrewela, et al., J Immunol, (1998), vol. 160, pp. 1067-1077.
Agrewala, et al., Eur J Immunol, (1994), vol. 24, pp. 2092-2097.
Nishimura, et al., Science, (2001), vol. 291, pp. 319-322.
Greenwald, et al., Immunity, (2001), vol. 14, pp. 145-155.
Salomon, et al., Annu Rev Immunol, (2001), vol. 19, pp. 225-252.
Krummel, et al., J Exp Med, (1996), vol. 183, pp. 2533-2540.

* cited by examiner

*Primary Examiner* — Sreeni Padmanabhan
*Assistant Examiner* — Jody Karol
(74) *Attorney, Agent, or Firm* — Birch, Stewart, Kolasch & Birch, LLP (57) ABSTRACT

The present invention relates to an isolated bioactive molecule Caerulomycin A, derivatives and analogs thereof as effective immunosuppressive agents. The immunosuppressive property of the compound is targeted in particular against the lymphocytes, $CD4^+$ T cells, $CD8^+$ T cells and B cells and in the production of IL-4 and IFN-$\gamma$ and antibodies. The compound operates through a mechanism by downregulating the expression of activation marker CD28 and upregulating the immunosuppressive marker CTLA-4. Caerulomycin A has previously been isolated from *Streptomyces caeruleus* and found to have useful antifungal activity. Prior to the present invention however, this compound had not been determined to have immunomodulatory activity.

20 Claims, 1 Drawing Sheet

USE OF BIPYRIDINE COMPOUND 'CAERULOMYCIN A' DERIVATIVES AND ANALOGS THEREOF AS IMMUNOSUPPRESSIVE AGENTS

FIELD OF INVENTION

The present invention relates to the use of the bipyridine compound Caerulomycin A, its derivatives and analogs as effective immunosuppressive agents. More particularly the present invention relates to an immunosuppressive agent that inhibits the naïve and activated lymphocytes (effectors), such as mitogen stimulated T and B-lymphocytes, CD4$^+$ T cells, Th1 and Th2 cells and in the production of IL-4 and IFN-γ.

The utility of the present invention is for treating diseases due to abnormal immune response induced by the activated T cells, such as autoimmune disease, inflammatory reaction, fibrosis or dysfunction caused by autoimmune disease or related disease thereof with tissue injury or infection, or allergic disease and suppressing the rejection of organ transplantation and graft versus host disease during transplantation. The compound, Caerulomycin A was isolated from a novel species of actinomycetes, *Actinoalloteichus spitiensis* sp. nov strain RMV-1378$^T$ having Accession No. MTCC 6194$^T$: DSM 44848$^T$: JCM 12472$^T$.

BACKGROUND OF THE INVENTION

Immune system of an organism has been developed with surveillance and defense mechanism by recognition and elimination of pathogenic foreign microorganisms such as bacteria and viruses. Therefore, the organism distinguishes own cells or tissues (self-antigens) from foreign microorganism (nonself-antigens), and does not respond to the self-antigens, or respond to them having the failure to mount immune response. Accordingly, the organism has developed an acquired immunity to eliminate nonself-antigens immediately and efficiently.

T lymphocytes (T cells) and B lymphocytes (B cells) are the primary cells of the adaptive arm of the immune system. Both are involved in acquired immunity and the complex interaction of these cells is required for the expression of the full range of effector and memory cells of the immune responses. T cells are specific for foreign antigens and their number must increase enormously in response for specific host defense.

Optimum activation of T cell depends on two discrete receptor-ligand recognition events. The major event is the interaction of T cell receptors (TCRs) with peptide-major histocompatibility complexes (PMHC) that are displayed on the surface of the antigen-presenting cell (APC) such as B cell, macrophage and dendritic cell. However, in the absence of a co-stimulatory signal, the TCR-pMHC interaction alone is insufficient for complete T cell activation and may result in either apoptotic death or prolonged unresponsiveness of the responding T cell (Agrewala et al. 1994, 1998).

It is the interaction of a family of related co-stimulatory receptors with their respective ligands that furnishes the second co-stimulatory signals (CD28, CD40L), which are required for efficient T cell activation. Moreover, a second, complementary set of co-stimulatory signals (CTLA-4, PD-1, BTLA) also provide negative signals that reduce the immune response and as such function to maintain the peripheral T cell tolerance to protect against autoimmunity (Nishimura et al. 2001, Greenwald et al. 2001).

The main co-stimulatory molecules expressed on the surface of T cells are CD28 and CTLA-4/CD152. CD28 is constitutively expressed on T cells. CD28 ligation enhances the magnitude and duration of T-cell responses; induces the anti-apoptotic gene BCL-X$_L$; increases cytokine secretion, particularly interleukin 2 (IL-2); enhances cell adhesion; facilitates reorganization of the T-cell plasma membrane upon binding to an APC; prevents anergy induction; and supports germinal center formation (Lanzavecchia et al. 1999). CD28 co-stimulation is necessary for the initiation of most T cell responses, and blockade of CD28 signaling results in a greatly reduced ability to respond to protein antigens, parasites and some viruses, and to generate germinal centers and mediate B-cell help. This has therapeutic implications; in that blockade of CD28 co-stimulation can be profoundly immunosuppressive, preventing induction of pathogenic T cell responses in autoimmune disease models and allowing for prolonged acceptance of allograft in models of organ transplantation (Salomon et al. 2001).

CTLA-4 (CD152) mediates such an inhibitory signal. CTLA-4 cross-linking by immobilized mAb or by soluble antibody cross-linked with a secondary antibody inhibited T cell responses induced by anti-CD3 and anti-CD28 antibodies (Krummel et al. 1996). Although CTLA-4 displays the common features of the CD28 family members, it is unique in several important ways. First, CTLA-4 has a markedly higher affinity for shared ligands B7-1 and B7-2 compared with CD28 ($K_d$ 0.2-0.4 ηm versus 4.0 µm), and a 40-100 fold higher avidity (van der Merwe et al. 1997).

Secondly, CTLA-4 has a unique expression pattern. Unlike CD28, CTLA-4 is not expressed constitutively on the cell surface of naïve T cells. CTLA4 is only expressed after the CD4$^+$ T cell becomes activated (2-3 days post APC-TCR engagement) and upon engagement with B7 molecules, transduces a negative signal to T cells. As the binding affinity of B7-1 and B7-2 for CTLA4 is 40-50× greater than for CD28, negative signaling would dominate on activated T cells, thereby terminating the immune response. CTLA-4 blockade in vivo enhances antigen-specific and anti-parasite responses, tumor rejection, autoimmune disease, and exacerbates graft rejection (Tivol et al. 1996, Chambers et al. 2001). In vitro, engagement of CTLA-4 results in inhibition of T cell proliferation, cytokine production and cell cycle progression (Chambers et al. 2001, Freeman et al. 2000).

CTLA-4 regulates peripheral tolerance by a number of different mechanisms. First, CTLA-4 regulates the activation of T cells by directly modulating T cell receptor signaling (i.e. TCR chain phosphorylation) (Lee et al. 1998) as well as biochemical signals (i.e. ERK activation). Second, recent studies have shown that the CD4$^+$ CD25$^+$ immunoregulatory T cells constitutively express CTLA-4 (Salomon et al. 2000). In fact, signaling via CTLA-4 is essential for the function of these cells (Takahashi et al. 2000). Thus, CTLA-4 may regulate signal transduction in the cells, which leads to differentiation into regulatory T cells; or alternatively, CTLA-4 engagement on the effector cells may alter signal transduction and subsequent cytokine production. Cross-linking of CTLA-4 induces secretion of the immunoregulatory TGF-β cytokine (Chen et al. 1998), which provides one possible mechanism of action for the CD4$^+$CTLA-4$^+$CD25$^+$ regulatory T cells.

Although the findings appear to suggest multiple functional effects of CTLA-4 in altering immune function, one of the models says that these apparently different activities are all related and the major effect of CTLA-4 is to alter the threshold of T cell activation by altering early events in TCR signaling. In fact, it has been demonstrated that treatment of T cells with cyclosporin A, a calcineurin inhibitor that modulates calcium mobilization, leads to the generation of a TGFβ- producing T cells that are similar to the CD4⁺CTLA-4⁺ CD25⁺ regulatory T cells (Prashar et al. 1995). Thus, the effects of CTLA-4 engagement whether directed at the inhibition of CD28 signaling, modulation of proximal TCR signals or down-stream effector pathways of T cell activation result in altered T cell differentiation and down regulation of immune responses. Hence, there exists a possibility of therapeutic potential of suppressing the exacerbation of diseases by regulating the expression of CTLA-4/CD28 on the surface of T cells by Caerulomycin A.

Many co-stimulatory molecules expressed on the surface of antigen presenting cells are known to date but B7-1 and B7-2 are the most potent and are responsible for the activation of T cells. Their interaction with CD28/CTLA-4 receptors expressed on T cell surfaces is quite crucial. Binding of CD28 to its ligands B7-1 and B7-2, delivers a co-stimulatory signal to T cell, enhancing their proliferation and cytokine secretion and preventing the induction of T cell anergy (Linsley et al. 1991). In contrast, the engagement of CTLA-4 by these same ligands results in down-regulation of the response that is essential for maintaining T cell homeostasis and self-tolerance (Tivol et al. 1995). B7-1 and B7-2, which share ~25% sequence identity, are type I transmembrane glycoproteins (Stamper et al. 2001). It is established phenomenon that interaction of CD28 and CTLA-4 with B7-ligands is critical for activation and inhibition of immune responses and tolerance respectively (Greenwald et al. 2005).

In summary, B and T cell responses depend on multiple and complex interdependent events. Because of the key role of B and T cell in immunity, their regulation is a major target for treating and/or preventing a large variety of diseases that require or benefit from an enhanced or reduced immunity, e.g. autoimmune diseases including type I diabetes, multiple sclerosis, asthma, arthritis, myasthenia gravis, lupus erythematosus, psoriasis, colitis, or rejection of transplanted organs, or immuno-deficiency diseases, and cancer. Therefore, there is a strong need for drugs capable of modulating the complex B and T cell responses for the purpose of treating and preventing numerous immunological disorders and diseases.

Successful organ transplantation requires effective physiological and pharmacological intervention of the immune system of an organ recipient. One approach to intervention of immune response in an organ transplant recipient, especially a recipient targeted for an allogenic graft, is by the use of immunosuppressive drugs. These drugs are used to prolong survival of transplanted organs in recipients in cases involving, for example, transplants of kidney, liver, heart, lung, bone marrow and pancreas.

There are several types of immunosuppressive drugs available for use in reducing organ rejection in transplantation. Such drugs fall within three major classes, namely: antiproliferative agents, anti inflammatory compounds and inhibitors of lymphocyte activation.

Examples of the class of cytotoxic or antiproliferative agents are azathioprine, cyclophosphamide and methotrexate. Drugs of the antiproliferative class may be effective immunosuppressives in patients with chronic inflammatory disorders and in organ transplant recipients by limiting cell activation and proliferation. These drugs which abrogate mitosis and cell division have severe cytotoxic side effects on normal cell populations which have a high turn-over rate, such as bone marrow cells and cells of the gastrointestinal (GI) tract lining. Accordingly, such drugs often have severe side effects, particularly, lymphopenia, neutropenia, bone marrow depression, hemorrhagic cystitis, liver damage, increased incidence of malignancy, hair loss, GI tract disturbances, and infertility.

A second class of immunosuppressive drugs for use in transplantation is provided by compounds having anti-inflammatory action. Representatives of this drug class are generally known as adrenal corticosteroids and have the advantage of not exerting globally systemic cytotoxic effects. These compounds usually act by preventing or inhibiting inflammatory responses, cytokine production, chemotaxis, neutrophil, macrophage or lymphocyte activation, or their effector function. Typical examples of adrenal corticosteroids are prednisone and prednisolone, which affect carbohydrate and protein metabolism as well as immune functions. Compounds of this class are sometimes used in combination with cytotoxic agents, such as compounds of the antiproliferative class because the corticosteroids are significantly less toxic. But the adrenal corticosteroids lack specificity of effect and can exert a broad range of metabolic, anti-inflammatory and immune effects. Typical side effects of this class include increased organ-recipient infections and interference with wound healing, as well as disturbing hemodynamic balance, carbohydrate and bone metabolism and mineral regulation.

A third class of immunosuppressive drugs for use in organ transplantation is provided by compounds, which are immunomodulatory and generally prevent or inhibit leukocyte activation. Such compounds usually act by blocking activated T-cell effector functions or proliferation, or by inhibiting cytokine production, or by preventing or inhibiting activation, differentiation or effector functions of platelet, granulocyte, B-cell, or macrophage actions. The cyclosporin family of compounds is the leading example of drugs in this class. Such compounds are polypeptide fungal metabolites, which have been found to be very effective in suppressing helper T-cells so as to reduce both cellular and humoral responses to newly encountered antigens. Cyclosporins alter macrophage and lymphocyte activity by reducing cytokine production or secretion and, in particular, by interfering with activation of antigen-specific CD4 cells, by preventing IL-2 secretion and secretion of many T-cell products, as well as by interfering with expression of receptors for these lymphokines on various cell types. Cyclosporin A, in particular, has been used extensively as an immunosuppressive agent in organ transplantation. Other microbial metabolites include cyclosporins such as cyclosporin B and cyclosporin G, and another microbial product known as FK-506. Cyclosporin A suppresses humoral immunity as well as cell-mediated reactions. Cyclosporin A is for organ rejection in kidney, liver, heart, pancreas, bone-marrow and heart-lung transplants. Cyclosporin A is also useful in the treatment of autoimmune and inflammatory diseases, including rheumatoid arthritis, Crohn's disease, Graves' disease, severe psoriasis, aplastic anemia, multiple-sclerosis, alopecia areata, penphigus and penphigoid, dermatomyositis, polymyositis, Behcet's disease, uveitis, pulmonary sarcocidiosis, biliary cirrhosis, myasthenia gravis and atopic dermatitis.

Cyclosporins possess several significant disadvantages. While cyclosporins have provided significant benefits in organ transplantation, cyclosporins are non-specific immunosuppressives. Desirable immune reactions may be reduced against foreign antigens. Tolerated dosages do not provide complete suppression of rejection response. Thus, immunologic reactions to transplanted tissue are not totally impeded, requiring concomitant treatment with prednisone, methylprednisolone, and/or other immunosuppression agents, including monoclonal antibodies such as anti-CD3 or anti-CD5/CD7. Cyclosporins can produce severe side effects in many organ recipients, and show host-variable effects on the liver, kidney, the central nervous system and gastro-intestinal tract. Significant among the adverse side effects are damage to the kidney and liver, hyperplasia of gum tissue, refractory hypertension and increased incidence of infections and malignancy.

Thus, the need remains for efficacious and selective immunosuppressive drugs for the treatment of autoimmune diseases and also in organ transplantation, especially for grafts between less-than-perfectly matched donor-recipient pairs. We therefore, present a proposal that takes a rationale approach to utilize Carulomycin isolated from the novel species of actinomycetes as an immunosuppressant for suppressing immune response. This and other objectives of the present invention, as well as additional inventive features, will be apparent from the detailed description provided herein. The inventors of the present invention have established that the optimum dosage of Caerulomycin A required in vivo was 5.0 mg/kg/body wt. The dosage of Caerulomycin A used in vitro experiments for inducing inhibition in the proliferation was 10 times lesser than the Cyclosporin A, which is a known immunosuppressant.

OBJECTS OF THE INVENTION

The main object of the present invention is thus to demonstrate that the compound Caerulomycin, it's derivative Caerulomycin A and other derivatives thereof including their pharmaceutically acceptable salts induce immunosuppression of the T and B lymphocytes.

Another object of the present invention is to demonstrate that Caerulomycin A suppresses mixed lymphocyte reaction.

Another object of the present invention is to demonstrate that Caerulomycin A inhibits the proliferation of the naïve $CD4^+$ T cells, antigen specific $CD4^+$ T cells and Th1 and Th2 cells.

Another object of the present invention is to demonstrate that Caerulomycin A retards the secretion of cytokines produced by T cells.

Another object of the present invention is to demonstrate that Caerulomycin A retards the production of antibodies by B cells.

Another object of the present invention is to demonstrate that Caerulomycin A modulates the expression of costimulatory molecules such as CD28 and CTLA-4 on T cells.

Still another objective of the present invention is to demonstrate that Caerulomycin A modulates the expression of costimulatory molecules such as B7-1 and B7-2 and MHC molecules on antigen presenting cells.

SUMMARY OF THE INVENTION

The present invention is directed to a fermentation process for producing and accumulating the compound Caerulomycin A, comprising cultivating a bacterium, *Actinoalloteichus spitiensis* sp. nov., having Accession No. MTCC 6194, under controlled aerobic fermentation conditions in an aqueous nutrient medium at about neutral pH, at a temperature ranging from about 25° C. to about 30° C., for from about 24 to about 168 hours, whereby isolable quantities of Caerulomycin A are present in the cultured broth.

The compound Caerulomycin A is isolated from the cultured broth by: a) separating the solids from the broth; b) extracting the filtrate broth with an immiscible extraction solvent; c) concentrating the extraction solvent to dryness; d) diluting the residue with saturated aqueous NaCl and 10% methanol 1:1 and partition with an immiscible solvent; e) removing the active materials from the aqueous alcohol fraction by partitioning with an appropriate solvent; f) combining and concentrating the recovered solvent phases containing the crude Caerulomycin A; and g) purifying the Caerulomycin A from the crude concentrated material by chromatographic technique.

The present invention further provides Caerulomycin A, as an effective immunosuppressive agent. The immunosuppressive property of the drug is targeted in particular against the T and B-cells and in the production of cytokines by these cells. The drug operates through a mechanism by downregulating the expression of activation marker CD28 and upregulating the expression of inhibition marker CTLA-4.

Caerulomycin A was first isolated from *Streptomyces caeruleus* and found to have strong antifungal activity and mild antibacterial activity (Funk and Divekar 1959). The anti-amoebic and phytotoxic properties of caerulomycin A have also been described (Chatterjee et al. and Chandran et al.). The disclosure of these properties is hereby incorporated herein by reference.

The invention provides the use of bipyridine compounds of general formula 1 as immunosuppressive agents.

formula 1

wherein,

X=—CH:NOR$_1$; —COOR$_1$; —CHO; —CH$_2$OR$_2$;

Y'H; OR$_3$;

R$_1$=H; C$_1$ to C$_{16}$ normal or branched chain alkyl;

R$_2$=H; C$_1$ to C$_{16}$ normal or branched chain alkyl; C$_1$ to C$_{16}$ normal or branched chain acyl;

R$_3$=H; methyl; ethyl; isopropyl; isobutyl;

and derivatives, esters, ethers and pharmaceutically acceptable salts thereof as immunosuppressive agents.

The present invention further provides use of caerulomycin A, (E)-4-methoxy-2,2'-bipyridine-6-carbaldehyde oxime of the formula 2, as an effective immunosuppressive agent formula 2

The invention also provides a process for the isolation of the compound of formula 2 from *Actinoalloteichus spitiensis* [MTCC 6194], the process comprising:

[a] culturing the strain of *A. spitiensis* [MTCC 6194] under controlled aerobic fermentation conditions in aqueous nutrient medium of neutral pH for a period of 30 to 100 hours at a temperature of 25 to 30 degree C. under shaking;

[b] sedimenting the cells obtained in step [a] to get a cell free supernatant;

[c] extracting the compound of formula 2 from the supernatant obtained in step [b] by known methods followed by purification thereof;

[d] optionally, characterizing the purified fraction using NMR, infrared and mass spectral data.

In an embodiment of the present invention, the compound is (E)-4-methoxy-2,2'-bipyridine-6-carbaldehyde oxime (Caerulomycin A) of the formula 2:

formula 2

In a further embodiment of the present invention, the compound is (E)-4-methoxy-2,2'-bipyridine-6-carbaldehyde O-methyl oxime of the formula 3:

formula 3

In still another embodiment of the present invention, the said compound is used at a dosage of 1.25 to 5.0 mg/kg body weight.

In an embodiment of the present invention, the said compound is 10 times more effective in inhibiting the immune response than cyclosporinA, which is a known immunosuppressive agent.

In an embodiment of the present invention, about 0.1 μg of the said compound per ml of the diluent inhibits about 90% to 97% of the immune cells within 48 hours.

In an embodiment of the present invention, the said compound inhibits the in vitro proliferation of T cells, B cells, Mixed Lymphocyte Reaction, Naïve $CD4^+$ T cells, antigen specific effector $CD4^+$ T cells, Th1 cells and Th2 cells.

In an embodiment of the present invention, the said compound inhibits the in vitro secretion of cytokines such as interferon-gamma (IFN-γ) and interleukin-4 (IL-4).

In an embodiment of the present invention, the said compound down regulates the expression of activation marker CD28 and up regulates the expression of inhibition marker CTLA-4 on T cells.

In an embodiment of the present invention, the said compound increases the expression of B7-1 and decreases the expression of B7-2 and MHC molecules on macrophages.

In an embodiment of the present invention, the said compound induces suppression of alfa-beta T cells and gamma-delta T cells, $CD4^+$ T cells and $CD8^+$ T cells, Th1 and Th 2 cells; naïve, effectors, memory and regulatory T cells.

In an embodiment of the present invention, the said compound induces suppression of B cells, mast cells, endothelial cells, NK cells, dendritic cells (myeloid DC, plasmacytoid DC, lymphoid DC, interstitial DC), monocytes, macrophage (splenic macrophages, peritoneal macrophages, alveolar macrophages, Kuffer's cells, Langerhans cells, osteoclasts, glial cells and all kinds of macrophages), epithelial cells, osteoblasts, eosinophils, basophils, granulocytes, platelets and megakaryocytes.

In an embodiment of the present invention, the said compound is useful for the treatment of autoimmune diseases like Addison's disease, autoimmune hemolytic anemia, Goodpature's syndrome, Graves' disease, Hashimoto's thyroiditis, idiopathic thrombocyopenia purpura, insulin dependent diabetes mellitus, Myasthenia Gravis, pernicious anemia, spontaneous infertility, multiple sclerosis, rheumatoid arthritis, systemic lupus erythematosus, spontaneous abortions.

In an embodiment of the present invention, the said compound induces immunosuppression and prevents graft rejection, graft versus host reaction and helps in transplantation.

In an embodiment of the present invention, the said compound is useful in treating neurological disorders such as epilepsy, stroke, cerebral ischemia, cerebral palsy, Alper's disease, Parkinson's disease, Alzheimer's disease, Huntington's disease, amyotrophic lateral sclerosis, multiple sclerosis, dementia with Lewy bodies, Rhett syndrome, neuropathic pain, spinal cord trauma, or traumatic brain injury, etc.

In an embodiment of the present invention, the said compound is isolated from a novel species of actinomycetes *Actinoalloteichus spitiensis* [MTCC 6194], which is isolated from the cold desert of Himalayas, India.

In an embodiment of the present invention, there is provided a process for the isolation of the compound of formula 2 from *Actinoalloteichus spitiensis* [MTCC 6194], the process comprising:

[a] culturing the strain of *A. spitiensis* [MTCC 6194] under controlled aerobic fermentation conditions in aqueous nutrient medium of pH 7.0-8.5 for a period of 30 to 100 hours at a temperature of 25 to 30 degree C. under shaking;

[b] sedimenting the cells obtained in step [a] to get a cell free supernatant;

[c] extracting the compound of formula 2 from the supernatant obtained in step [b] by known methods followed by purification thereof;

[d] optionally, characterizing the purified fraction using NMR, infra-red and mass spectral data.

In an embodiment of the present invention, the cells are cultured preferably for a period of 40-70 hours.

In an embodiment of the present invention, the cells are cultured preferably at a temperature of 28-30 degree C.

In an embodiment of the present invention, the cells are cultured preferably at a pH of 7-8.5.

In an embodiment of the present invention, the recovery of the compound of formula 2 is about 150 mg/l of the culture broth.

In an embodiment of the present invention, the active fraction obtained is useful as an immunosuppressive agent.

In an embodiment of the present invention, there is provided a method for treating autoimmune diseases comprising administering to the patient 1.25 to 5.0 mg of the compound of the general formula 1, per kg body weight.

In an embodiment of the present invention, the compound is administered in a single dosage form daily for 3 days.

In an embodiment of the present invention, there is provided an immunosuppressive pharmaceutical composition useful for immunosuppression comprising 1.25 to 5.0 mg of the compound of the general formula 1 along with pharmaceutically acceptable diluents, additives and/or carriers.

BRIEF DESCRIPTION OF THE DRAWINGS

FIG. 1: Different groups, each comprising five animals were immunized with OVA, followed by CaeA administration daily for 7 days before mice were sacrificed. Splenocytes ($2\times10^5$ cells/well) were isolated and cultured in vitro with 100 μg/ml OVA and varied doses of CaeA. After 72 h, [$^3$H]-thymidine was added, and its incorporation was measured 16 h later. The control cultures consisting of cells cultured in medium alone showed 3789±359 cpm, cells+OVA showed 16387±431 cpm and cells obtained from the animals immunized with PBS-ethanol and cultured in-vitro with OVA showed 13801≅587 cpm.

FIG. 2: In another set of experiment, three different groups were immunized with OVA followed by administration of CaeA (25 μg/mice) in one of the group and Alcohol (vehicle control) in another group, daily for 7 days before mice were sacrificed. Splenocytes ($2\times10^5$ cells/well) were isolated and cultured in vitro alone or with OVA 100 and 200 μg/ml (1.2). Each point represents the mean±SEM of triplicate determinations from one of the three representative experiments.

DETAILED DESCRIPTION OF THE INVENTION

The systematic study of the products from actinomycetes and fungi has led to the development of immunosuppressive drugs such as cyclosporin A (CsA), FK506 (tacrolimus) and rapamycin (sirolimus). These drugs not only exert potent antifungal effects but are also used as potential immunosuppressants. By taking into consideration this point we started our study for screening of bioactive compounds with antifungal activities by isolating various microbes from soil and water samples from the cold Himalayan region of Kaza and Spiti in Himachal Pradesh. Polyphasic characterization of the strain RMV-1378$^T$, isolated from cold desert of the Himalayas, India, clearly confirmed that the strain belong to the genus *Actinoalloteichus*. Physiological and biochemical tests allowed genotypic and phenotypic differentiation of the strain RMV-1378$^T$ from its closest phylogenetic relative. Analysis of 16S rDNA sequence revealed that the isolate is very closely related to *Actinoalloteichus cyanogriseus* with similarity of 99%. However, results of DNA-DNA hybridization, showed low genomic relatedness with *Actinoalloteichus cyanogriseus* (51%). Therefore, we proposed that the isolate be classified as a new species of *Actinoalloteichus*, for which we proposed the name *Actinoalloteichus spitiensis* sp. nov. The strain RMV-1378$^T$ has been deposited in Microbial Type Culture Collection and Gene Bank (MTCC), India under accession number MTCC 6194$^T$ and type strain RMV-1378$^T$ has also been deposited in Japan Collection of Micro-organisms (JCM), Japan under accession number JCM 12472$^T$ and German Collection of Microorganisms and Cell Cultures (DSMZ) Germany, under accession number DSM 44848$^T$. The active ingredient isolated from strain RMV-1378 was characterized based on nuclear magnetic resonance (NMR), infrared (IR) and mass spectral data. The identified compound was (E)-4-methoxy-2,2'-bipyridine-6-carbaldehyde oxime. The data corresponded well with the already reported data of Caerulomycin A (Divekar et al. 1967).

Following are the major characteristics of the isolated strain *Actinoalloteichus spitiensis:* a) An actinobacterial strain, RMV-1378$^T$, forms branching, non-ragmenting vegetative hyphae and do not produce diffusible pigments. Neither aerial mycelium nor spore formation is observed.

b) The G+C content of the DNA was 72.0 mol %.

c) The strain has chemotaxonomic characteristics typical of the genus *Actinoalloteichus* and is closely related (99.3% 16S rRNA gene sequence similarity) to *Actinoalloteichus cyanogriseus*, currently the only *Actinoalloteichus* species with a validly published name. However, the results of DNA-DNA hybridization experiments showed 51.9% relatedness with the type strain of *A. cyanogriseus*.

d) On the basis of the above data and the physiological and biochemical distinctiveness of RMV-1378$^T$ (=MTCC 6194$^T$=JCM 12472$^T$=DSM 44848$^T$, this strain is classified as the type strain of a novel species of *Actinoalloteichus*, for which the name *Actinoalloteichus spitiensis* sp. nov. is accorded.

The Microbial Type Culture Collection & Gene Bank (MTCC), a National Facility, was established in 1986 and is sponsored jointly by the Department of Biotechnology (DBT), Govt. of India and the Council of Scientific and Industrial Research (CSIR). This is a well-equipped modern facility housed at the Institute of Microbial Technology (IMTECH), Chandigarh. MTCC is an affiliate member of the World Federation of Culture Collection (WFCC) and is registered with World Data Centre for Microorganisms (WDCM: Reg. No. 773). Main objectives of this National Facility are to act as a depository, to supply authentic microbial cultures and to provide related services to scientists working in research institutions, universities and industries. On Oct. 4, 2002 MTCC was recognised by WIPO (Geneva) as an International Depositary Authority [IDA] in India, for the deposit of microorganisms under the Budapest Treaty.

Fermentation of the Producing Organism

Caerulomycin A is produced in this invention by the controlled fermentation of a microorganism. This microorganism is preferably grown in an aqueous nutrient medium, under aerobic and mesophilic conditions, preferably between 25° C. and 35° C. at a pH ranging between about 6.0 and 8.0. The length of the fermentation typically ranges between 24 h and 168 h, preferably between 24 h and 96 h. A good production can be obtained at 30° C. and a pH 7.0 to 8.5. The nutrient medium employed should preferably be composed of any suitable nitrogen source such as protein hydrolysates, or protein and/or isolated amino acids, or any ammonium and/or nitrate source; as source of carbon any assimilable carbohydrate and/or fat, and may also contain salts such as sodium chloride, sodium carbonate, sodium bicarbonate, potassium chloride, magnesium chloride, calcium carbonate, etc.

With medium containing glucose 5.4 g, yeast extract 4.8 g, malt extract 8.5 g, CaCO$_3$ 3.0 g, distilled water 1000 ml, pH 7.2 and incubation temperature of 28° C., good production of Caerulomycin A occurs.

It must be appreciated that the above-mentioned medium is merely an example of a medium suitable for the production of Caerulomycin A by strain of *Actinoalloteichus spitiensis* sp. nov. It is believed that a wide range of nutrient media may be substituted for the one disclosed herein, with good growth and production resulting therefrom.

All cultures and fermentations must be conducted in sterile media and conditions. To start fermentation, it is necessary to seed it with an inoculum grown in a medium similar to the one already described for the fermentation. The percentage of inoculum typically needed ranges between 1 and 10%; 10% being typically preferred.

Isolation and Purification of Caerulomycin A from Broth

Isolation and purification of the Caerulomycin A produced by fermentation is typically conducted using a combination of extraction and chromatographic techniques. A preferred sequence of steps is as follows:

Extract the filtrate broth with an immiscible solvent such as ethyl acetate. Combine these extracts and concentrate to dryness in vacuo. Dilute the residue extract with NaCl 10%/ methanol (1:1) and partition it with an immiscible solvent such as hexane which is capable of removing the lipids. Remove the active materials from the aqueous alcohol fraction by partitioning with an appropriate solvent such as ethyl acetate. The recovered solvent phases constitute crude Caerulomycin A.

Further separation and purification of Caerulomycin A from the crude extract can be affected by the use of the proper combination of chromatographic techniques, including, for example, column chromatography (CC), high performance flash chromatography, preparative medium pressure liquid chromatography (MPLC) and thin layer chromatography (TLC). Fractionation may be guided by immunosuppressive activities.

On the basis of detailed analysis of their various spectral characteristics, the pure compound was identified as Caerulomycin A.

In an embodiment of the present invention Caerulomycin A suppressed the activity of mitogen-stimulated T and B-lymphocytes. The lymphocytes were stimulated with T cell mitogen concanavalin A (Con A) and B cell mitogen lipopolysaccharide (LPS) and different doses of Caerulomycin A (0.0003-0.1 μg/ml). As compared to the cells cultured with mitogens alone, Caerulomycin A induced significant decrease in mitogen-induced proliferation.

In another embodiment of the present invention Caerulomycin A also showed in vitro suppression of MLR reaction, naïve $CD4^+$ T cells, antigen specific $CD4^+$ T cells, and Th1 and Th2 cells. Caerulomycin A activity was compared with a well-known immunosuppressive drug cyclosporin A (CsA). It was observed that there was a dose dependent inhibition in MLR by both the drugs. Interestingly, Caerulomycin A was effective in inhibiting similar amount of proliferation using a 10 fold lesser dose than CsA.

In still another embodiment of the present invention, Caerulomycin A also inhibited in vivo proliferation of the antigen specific T cells. Antigen (ovalbumin: 100 μg/ml) was emulsified in Freund's complete adjuvant and was injected intraperitoneally in different groups (5 mice/group). Different groups of ovalbumin-primed animals were daily-injected different doses of Caerulomycin A (25, 50, 75, 100 μg/100 μl/mice). After seven days, mice were sacrificed, splenocytes from each group were separately pooled, and in vitro proliferation was monitored.

In yet another embodiment of the present invention, Caerulomycin A significantly suppressed the secretion of IL-4 and IFN-γ.

In another embodiment of the present invention, Caerulomycin A induces immunosuppression by down regulating CD28 and upregulating CTLA-4 expression. It is established that CTLA-4 delivers immunosuppressive signals. In contrast, CD28 conveys activation signals to T cells. It was observed that Caerulomycin A not only significantly enhanced the expression but also the percentage of CTLA-4/CD4 positive T cells and decreased the expression and percentage of CD28/CD4 positive T cells. Similar results were noticed in the case of non-$CD4^+$ T cells.

In another embodiment of the present invention, Caerulomycin A inhibited the secretion of IgG1 and IgG2a type of antibodies.

In yet another embodiment of the present invention, Caerulomycin A upregulated B7-1 but downregulated B7-2 expression on macrophages. Many costimulatory molecules are expressed on the surface of APC's but B7-1 and B7-2 are the most potent. Their interactions with CD28/CTLA-4 receptors expressed on T cell surfaces are crucial for the proper regulation of T cell activity. We therefore monitored the expression of their ligands B7-1 and B7-2. B7-1 binds to both CTLA4 and CD28 more strongly than does B7-2. However, when the relative interactions are directly compared, B7-1 favors binding to CTLA-4 over CD28 by 20-fold, whereas B7-2 only favors CTLA-4 over CD28 by about 8-fold. In view of the above-mentioned findings, the potent role of Caerulomycin A as an imunosupppression agent can be viewed by a mechanism of enhancement of the expression of CTLA-4 on T cells and B7-1 on APC.

Caerulomycin A Induces Immunosuppression of Lymphocytes

Caerulomycin A Induces Immunosuppression of Mixed Lymphocyte Reaction (MLR)

The MLR was performed in 96-well tissue culture plates, with each well containing $4\times10^5$ BALB/c splenocytes (responder cells) and $4\times10^5$ γ-irradiated (3000R) C57BL/6J splenocytes (stimulator cells) in 200 μl RPMI/FCS-10% medium and with various concentrations of Caerulomycin A (1-0.0125 μg/ml) and Cyclosporin A (0.0125-10 μg/ml). The control cultures consisting of BALB/c splenocytes in medium alone, γ-irradiated C57BL/6J splenocytes and BALB/c splenocytes+γ-irradiated C57BL/6J splenocytes were also kept. After 4 days, the cultures were pulsed with 1 μCi of [$^3$H]-thymidine and harvested 16 h later by a Skatron cell harvester. Radioactivity incorporated was measured by liquid scintillation counting and data expressed as mean counts per minute (cpm).

Caerulomycin A substantially reduced the MLR reaction. Caerulomycin A was ten times more potent than Cyclosporin A in suppressing the MLR reaction. No significant level of [$^3$H]-thymidine incorporation was observed in the control cultures containing cells only, cells cultured with Caerulomycin A (in the absence of either ConA or LPS or anti-CD3Ab or APCs). In all assays, Caerulomycin A worked in a dose dependent manner.

Caerulomycin A Induces Immunosuppression of Lymphocytes Stimulated with T Cell and B Cell Mitogens Splenocytes of BALB/c mice were cultured ($5\times10^4$ cells/well) in 200 μl RPMI/FCS-10% medium and stimulated with different concentrations of either ConA (1 μg/ml and 2 μg/ml) or LPS (5 μg/ml and 10 μg/ml) and Caerulomycin A (0.0003-0.1 μg/ml). The control cultures consisting of splenocytes incubated with medium alone, ConA and DMSO. After 48 h, the cultures were pulsed with 0.5 μCi of [$^3$H]-thymidine and harvested 14 h later by automatic cell harvester (Skatron, Tranby, Norway). Radioactivity incorporated was measured by liquid scintillation counting and data are expressed as mean counts per minute (cpm).

As compared to the cells cultured with ConA alone, Caerulomycin A induced significant decrease in the proliferation of ConA (1.0 and 2.0 μg/ml) stimulated cells. We also stimulated splenocytes with LPS (5 and 10 μg/ml). Interestingly, Caerulomycin A could also suppress the proliferation of the cells stimulated with LPS (5 and 10 μg/ml). We observed that the doses (0.05 and 0.1 μg/ml) of Caerulomycin A induced potent inhibition in the proliferation.

Caerulomycin A Induces Immunosuppression of $CD4^+$ T Cells Obtained from the Antigen-Primed Animals A single cell suspension of mice splenocytes obtained from OVA-CFA primed mice. The red blood cells were depleted by treatment with hemolytic Gey's solution. The adherent cells were removed by plating onto plastic Petri plates for 2 h at 37° C. and 7% $CO_2$. The non-adherent cells were loaded ($1\times10^6$ cells/ml) onto the nylon wool column and incubated for 90 min at 37° C. After the incubation period, warm RPMI was passed into the column to elute T lymphocytes. The T cells were washed with RPMI and incubated with anti-Mac3 (TIB- 168), anti-IA$^d$ (MKD6), anti-dendritic cell (TIB-227), anti-IgM and anti-CD8 Abs for 45 min at 4° C. The cells were washed with RPMI and incubated with baby rabbit complement for 30 min at 37° C. The cells were washed three times with RPMI and used for the proliferation assay. The purity of the cells was analyzed by flow-cytometry of the cells stained with anti-CD3 and CD4 Abs.

CD4$^+$ T cells were purified from the OVA-FCA injected mice and stimulated with antigen-pulsed and γ-irradiated splenocytes. As compared to antigen stimulated CD4$^+$ T cells, addition of Caerulomycin A in the cultures significantly suppressed the proliferation.

Caerulomycin A Induces Immunosuppression of Th2 Cells.

The proliferation of Th2 clones was measured using cells harvested on 7-9 days after stimulation with antigen pulsed splenocytes. The dead cells were removed by ficoll-histopaque. Th2 clones ($5 \times 10^4$ cells/well) were either stimulated with anti-CD3 Ab (0.1 μg/ml and 0.5 μg/ml) or incubated with γ-irradiated (3000 R) syngeneic splenocytes ($5 \times 10^5$ cells/well) and conalbumin (100 μg/ml) in 200 μl RPMI/FCS-10% medium and with various concentrations of Caerulomycin A (0.00625-0.1 μg/ml). The control cultures consisting of Th2 cells incubated with conalbumin alone and γ-irradiated syngeneic splenocytes (no antigen) were also kept. The cultures were kept in a flat bottom 96 well microtitre plate and the cells were incubated at 37° C. and 7% $CO_2$. After 48 h, the cultures were pulsed with 0.5 μCi of [$^3$H]-thymidine and harvested 16 h later. Radioactivity incorporated was measured by liquid scintillation counting and data are expressed as mean counts per minute (cpm).

Caerulomycin A was added into the cultures of Th2 cells stimulated either with anti-CD3 Ab or conalbumin pulsed and γ-irradiated splenocytes. As observed in the case of mitogen stimulated lymphocytes and antigen specific T cells, Caerulomycin A also substantially restricted the proliferation of Th2 clones in both the stimulatory conditions.

Caerulomycin A Induces Immunosuppression of Th1 Cells

Th1 cells ($1 \times 10^4$ cells/well) were stimulated with anti-CD3 Ab (10 μg/ml) and different doses Caerulomycin A. After 24 h, [$^3$H]-thymidine was added, and its incorporation was measured 8 h later.

Caerulomycin A also inhibited the proliferation of Th1 cells (3DO.54.8). This feature was observed irrespective of whether Th1 cells were stimulated with anti-CD3 Ab.

Caerulomycin A Suppresses the Production of IL4 and IFN-γ

OVA (2 mg/ml) was dissolved in PBS (0.01 M, pH 7.2) and emulsified in Freund's complete adjuvant (FCA). Emulsion (100 μl) was then injected intraperitoneally in a group consisting of 5 BALB/c mice. The control group was injected with PBS alone. After seven days, mice were sacrificed and splenocytes were pooled and used for proliferation and cytokine assays. Splenocytes ($5 \times 10^5$ cells/well) were cultured with OVA (200 μg/ml) in 200 μl RPMI/FCS-10% medium and with various concentrations of Caerulomycin A (0.0003-0.1 μg/ml). The control cultures consisting of splenocytes incubated with different concentrations of Caerulomycin A (no OVA), OVA and medium were also kept. The culture supernatants were collected after 48 h and cytokines were measured by ELISA.

It was observed that Caerulomycin A (0.05-0.1 μg/ml) significantly suppressed the secretion of IFN-γ by OVA-specific T cells. Caerulomycin A failed to induce any change in the production of IL-10. It was also interesting to notice that Caerulomycin A suppressed the release of IL-4 by D10G4.1 Th2 clones stimulated either with anti-CD3 Ab (0.1 and 0.5 μg/ml) or conalbumin pulsed APC.

Caerulomycin A Inhibits the In Vivo Proliferation of Antigen Specific T Cells

OVA (2 mg/ml) was dissolved in PBS (0.01 M, pH 7.2) and emulsified in Freund's complete adjuvant (FCA). Emulsion (100 μl) was then injected intraperitoneally (i.p.) in 7 groups, comprising 5 BALB/c mice in each set. Four groups of animals were injected intraperitoneally daily with Caerulomycin A (25, 50, 75, 100 μg/100 μl/mice). The control groups were immunized intraperitoneally with 100 μl each of PBS and ethanol-PBS. After seven days, mice were sacrificed and splenocytes were isolated and pooled for in vitro proliferation.

The cells isolated from the antigen-primed animals that were injected. Caerulomycin A showed substantial inhibition in the proliferation as compared to the animals that were not administered drug.

Kinetics of the Effect of Caenulomycin A on the Proliferation of Th2 Clones

Th2 clones ($5 \times 10^4$/well) were stimulated with anti-CD3 Ab (0.5 μg/ml). Caerulomycin A (0.05 μg/ml) was added either at the initiation of the cultures (time 0) or at various time points (4 h-48 h) After 48 h of the cultures, [$^3$H]-thymidine was added, and its incorporation was measured 12 h later.

Caerulomycin A showed maximum inhibitory (77-90%) effect on Th2 cells if added before 16 h of the initiation of the cultures. The inhibitory effect of Caerulomycin A was retained in the cultures when added even after 42 h (56%). However, the response was lesser as compared to when the drug was added before 16 h. Thus, indicating that Caerulomycin A not only exerts its inhibitory effect on the activation events but also on the later stages of cell division.

Effect of Caerulomycin A on the Calcium Dependent (PMA+ Lonomycin) Pathway

Cells were seeded at $5 \times 10^4$ cells/well in flat-bottom 96-well plates. The various stimuli and Caerulomycin A were added at the initiation of the cultures. After 48 h, [$^3$H]-thymidine (1 μCi/well) was added, and its incorporation was measured 12 h later. It was observed that Caerulomycin A significantly inhibited the proliferation of calcium dependent pathway.

Caerulomycin A Induces Upregulation of CTLA-4 and Downregulation CD28 Expression CD28 and CTLA-4 expression was detected on the surface of the resting and ConA activated CD4$^+$ T cells by flow cytometric analysis. Briefly, the splenocytes ($3 \times 10^6$ cells/well) were activated with OVA (200 μg/ml) or ConA (1 μg/ml and 2 μg/ml) and were incubated in the presence of different concentrations of Caerulomycin A (0.0125-0.45 μg/ml). The cultures were harvested after 24, 48, 72 and 96 h and cells were stained for the expression of CD4, CD28 and CTLA-4. Further, cultures were also set where Caerulomycin A was added after 24 h and 48 h of the initiation of cultures and the cells were stained after incubating further for 24 h. The cells were harvested and 3-color staining was done using PE (Phycoerythrin) conjugated anti-CD4 Ab, FITC (Fluorescein isothiocyanate) conjugated anti-CTLA-4, and Cy (Cychrome) conjugated CD28 Abs. The cells from each suspension were acquired on CELLQUEST software of FACScan (Becton Dickinson, Mountain View, Calif.). Debris in the cell suspension was excluded from the analysis by suitable gating that allowed the collection of data only from these light scattering events (i.e. cells) of a size consistent with lymphocytes. The analysis for the mean fluorescence intensity (MFI) was done on histograms where abcissa and ordinate denote log fluorescence and relative cell count, respectively.

Since we observed Caerulomycin A mediated immunosuppression, therefore it became quite necessary to look into the mechanism of its action. It is very well established that CTLA-4 delivers immunosuppressive signals to T cells and CD28 delivers stimulatory signals for the proliferation. We therefore became curious to monitor the expression of CTLA-4 and CD28 on CD4$^+$ T cells. It was interesting to observe that Caerulomycin A not only significantly enhanced the expression but also the percentage of CTLA-4 positive cells. In contrast, it decreased the expression and percentage of CD28. Similar results were noticed in the case of non CD4$^+$ T cells. Thus, indicating that Caerulomycin A suppresses the proliferation and cytokine secretion by CD4$^+$ T cells by enhancing the expression of CTLA-4 and inhibiting the expression of CD28. Further, it was observed that Caerulomycin A did not exhibit any significant change either in the expression or percentage change in LFA-1 positive cells.

Expression of CD69 on Mouse Thymocytes

The expression of CD69 was detected on the surface of thymocytes in the presence of Caerulomycin A. Thymocytes were obtained from 3-4 weeks old BALB/c mice. Thymocytes ($4 \times 10^6$ cells/well) were stimulated with 1 µg/ml and 5 µg/ml of ConA for 24 h in the presence and absence of Caerulomycin A at 37° C. The cells were stained with PE labeled anti-mouse CD69 Ab. The stained cells were acquired on a FACScan as mentioned in the case of CD28/CTLA-4.

It is known that CD69 is an activation marker on T cells and thymocytes. Interestingly, after addition of Caerulomycin A there was no change in the expression of CD69 on the thymocytes.

Caerulomycin A Modulates the Expression of Co-Stimulatory Molecules B7-1, B7-2 and CD40 on Macrophages The expression of B7-1 and B7-2 was detected on the surface of peritoneal macrophages incubated with different concentrations of Caerulomycin A (0.05-0.1 µg/ml). Peritoneal macrophages were harvested from BALB/c mice inoculated 4 days previously with 2-3 ml of thioglycolate. The cells were washed with BSS. The macrophages were obtained by adhering for 1 h at 37° C. on plastic Petri dishes followed by washing several times in cold BSS. The macrophages ($1 \times 10^6$) were stimulated with 10 µg/ml of LPS for 24, 48 and 72 h in the presence and absence of Caerulomycin A (0.05-0.1 µg/ml) at 37° C. and 7% $CO_2$. Then the cells were harvested and stained with their respective antibodies. Briefly, the cells were centrifuged (1200×g, 4° C., 5 min) and the supernatant was aspirated. The cells were washed 3× with 1% BSA, 0.1% sodium azide in PBS. In the first step, the cells ($1 \times 10^6$) were incubated with biotinylated anti-mouse B7-1, CD40 and I-A$^d$ (1 µg/100 µl) Abs for 45 min at 4° C. In the next step cells were stained with streptavidin FITC (0.5 µg/100 µl) or PE conjugated anti-mouse B7-2 (0.5 µg/100 µl) Abs and incubated for 45 min. Usual steps of washing were followed at each step. Finally the cells were washed five times and fixed in paraformaldehyde. The stained cells were acquired on a FACScan as mentioned for CD28/CTLA-4. Since the antigen presenting cells express B7-1 and B7-2, which are the ligands of CTLA-4 and CD28. Interestingly, Caerulomycin A enhanced the expression of B7-1 and decreased the display of B7-2 molecule. In contrast, it increased the expression of B7-2 but no major change was observed in the case of B7-1 expression on J774 we also evaluated the role of Caerulomycin A on the expression of another co stimulatory molecule CD40. Slight increase in the expression of CD40 was observed after 72 h.

Caerulomycin A Down Regulates the Expression of IA$^d$ on Macrophages

The expression of IA$^d$ was detected on the surface of peritoneal macrophages incubated with different concentrations of Caerulomycin A (0.05-0.1 µg/ml). Peritoneal macrophages were harvested from BALB/c mice inoculated 4 days previously with 2-3 ml of thioglycolate. The cells were washed with BSS. The macrophages were obtained by adhering for 1 h at 37° C. on plastic Petri dishes followed by washing several times in cold BSS. The macrophages ($1 \times 10^6$) were stimulated with 10 µg/ml of LPS for 24, 48 and 72 h in the presence and absence of Caerulomycin A (0.05-0.1 µg/ml) at 37° C. and 7% $CO_2$. Then the cells were harvested and stained with their respective antibodies. Briefly, the cells were centrifuged (1200×g, 4° C., 5 min) and the supernatant was aspirated. The cells were washed 3× with 1% BSA, 0.1% sodium azide in PBS. In the first step, the cells ($1 \times 10^6$) were incubated with biotinylated anti-mouse I-A$^d$ (1 µg/100 µl) Abs for 45 min at 4° C. In the next step cells were stained with streptavidin FITC (0.5 µg/100 µl) and incubated for 45 min. Usual steps of washing were followed at each step. Finally the cells were washed five times and fixed in paraformaldehyde. The stained cells were acquired on a FACScan as mentioned for CD28/CTLA-4. It is of interest to mention here that Caerulomycin A down regulated the expression of IA$^d$. This may indicate that Caerulomycin A may inhibit the processing and presentation of antigen by APC.

Immunization Method for In Vivo Proliferation

Ovalbumin (3 mg/ml) was dissolved in PBS (pH 7.2) and emulsified in Freund's complete adjuvant (FCA). Emulsion (100 µl) was then injected intraperitoneally (i.p.) in different groups, comprising 5 BALB/c mice in each set. Four groups of animals were injected intraperitoneally daily with caerulomycin A (25, 50, 75, 100 µg/100 µl/mice). The control groups were immunized intraperitoneally with ethanol-PBS.

OVA-Induced Lymphoproliferation and Cytokine Estimation

After seven days, mice were sacrificed and splenocytes were pooled and used for proliferation assays. Splenocytes ($2 \times 10^5$ cells/well) were cultured with OVA (100 µg/ml) in 200 µl RPMI/FCS-10% medium and with various concentrations of caerulomycin A (0.1-0.0003 µg/ml). The control cultures consisting of splenocytes incubated with different concentrations of caerulomycin A (no OVA), OVA and medium were also kept. After 72 h, the cultures were pulsed with 1 µCi of [$^3$H]-thymidine and harvested 14 h later. Radioactivity incorporated was measured by liquid scintillation counting and data are expressed as mean counts per minute (cpm).

Caerulomycin A Inhibits the In Vivo Proliferation of Antigen Specific T Cells.

Figure 1:
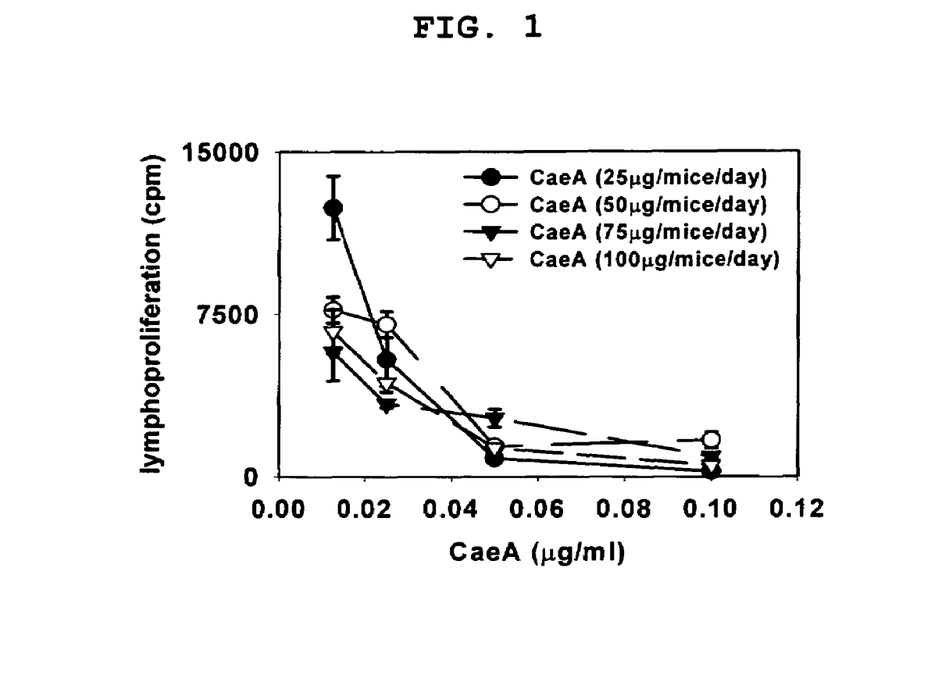
FIGS. 1 and 2: CaeA inhibits the proliferation of OVA specific T cells in-vivo.
Figure 2:
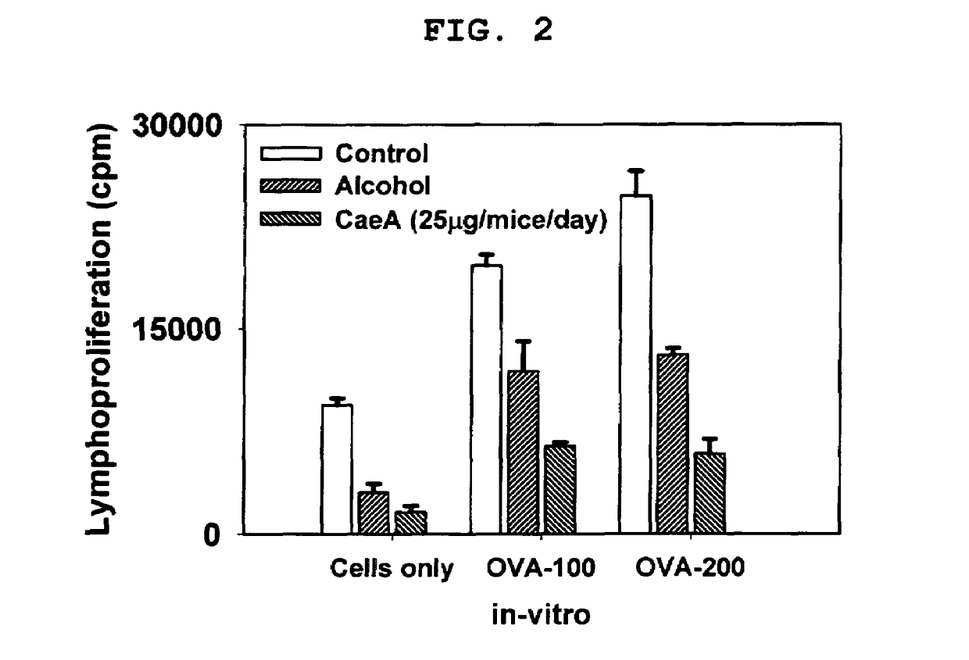

The mice were administered with different doses of caerulomycin A for 7 days (FIG. 1). The animals were sacrificed and splenocytes were cultured in vitro with antigen and different concentrations of caerulomycin A (0.00625-0.10 µg/ml). Interestingly, cells isolated from the animals injected with all the four concentrations (25-100 µg/mice/day) of caerulomycin A showed substantial inhibition in the proliferation as compared to the animals that were not administered with drug (FIG. 1). The decrease in the proliferation was observed in a dose dependent manner. Nearly complete inhibition was observed when cells were incubated with 0.10 µg/ml of caerulomycin A. In another set of experiments, the cells were isolated from the animals primed with antigen and later on administered either PBS-ethanol or caerulomycin A (25 µg/mice/day) for 7 days (FIG. 2). The cells isolated from the mice injected with caerulomycin A showed significant level of retardation in the growth as compared to the cells isolated from the animals immunized with PBS-ethanol (FIG. 2).

The following examples are given by way of illustration of the present invention and therefore should not be construed to limit the scope of the present invention.

Example 1

Preparation by Fermentation of Caerulomycin A

A. Inoculum Preparation

Prepare a seed culture inoculating test tubes with 5 ml of a medium having the following composition: glucose 5.4 g, yeast extract 4.8 g, malt extract 8.5 g, $CaCO_3$ 3.0 g per liter in distilled water. Adjust pH to 7.2, sterilize the broth and after cooling add a frozen culture of *Actinoalloteichus spitiensis* sp. nov. Cultivate the bacterium at 28° C. for 30 hours with orbital agitation at 200 rpm. Inoculate aseptically with 7.5 ml of the above culture in a shaking flask of 1000 ml capacity with 100 ml of sterile culture medium as defined below: glucose 5.4 g, yeast extract 4.8 g, malt extract 8.5 g, $CaCO_3$ 3.0 g per liter in distilled water. Adjust pH to 7.0 with an alkali solution. Cultivate the bacterium at 28° C. for 30 hours with orbital agitation at 200 rpm.

B. Fermentation

Sterilize at 122° C. for 30 minutes a fermenter of 7 liters capacity with 5 liters of the production medium described as below: glucose 5.4 g, yeast extract 4.8 g, malt extract 8.5 g, $CaCO_3$ 3.0 g per liter in distilled water. Inoculate the fermenter with 500 ml of the second stage inoculum. Incubate the fermentation culture at 28° C. with an agitation of 220 rpm with 1 v/v/m aeration.

C. Isolation

After completion of the cultivation, remove the solids by centrifugation. Extract the supernatant portion (4.8 liters) twice with 2.5 liters of ethyl acetate. Desiccate the combined organic phases with sodium sulfate, filter and concentrate to dryness under vacuum. Dissolve the crude residue in 80 ml of water:methanol (1:1) which was defatted by partitioning twice with 50 ml of hexane. Extract the water/alcohol fraction twice with 50 ml of ethyl acetate. Concentrate the organic solvent in an evaporator yielding a crude residue containing Caerulomycin A.

Example 2

Separation of Caerulomycin A from Crude Extracts

Dissolve the crude residue in 5 ml acetone and chromatograph on silica gel (32-63 μM) by a High Performance Flash Chromatography System (Horizon HPFC system, Biotage, USA) using a mixture of toluene/acetone 75:25 as the eluting solvent. Combine similar fractions on the basis of TLC analysis, using chloroform-methanol-20% aqueous ammonia 95:4:1 as the mobile phase.

Examples establishing the role of Caerulomycin A [isolated from a novel species of *Actinoalloteichus*] in inducing immunosuppression based on the following:

- Splenocytes of BALB/c mice were stimulated with either ConA (1 μg/ml and 2 μg/ml) or LPS (5 μg/ml and 10 μg/ml) and were cultured with different concentrations of Caerulomycin A (0.0003-0.1 μg/ml). After 48 h, the cultures were pulsed with 0.5 μCi of [$^3$H]-thymidine and harvested 14 h later by automatic cell harvester. Radioactivity incorporated was measured by liquid scintillation counting.
- Antigen ovalbumin (100 μg/ml) emulsified in Freund's complete adjuvant was injected in a group consisting of 5 BALB/c mice. The control group was injected with PBS alone. After seven days, mice were sacrificed and splenocytes were pooled and used for proliferation and cytokine assays. Splenocytes were cultured with ovalbumin (200 μg/ml) in 200 μl RPMI/FCS-10% medium and with various concentrations of Caerulomycin A (0.0003-0.1 μg/ml). After 72 h, the cultures were pulsed with 1 μCi of [$^3$H]-thymidine and harvested 14 h later. Radioactivity incorporated was measured by liquid scintillation. The culture supernatants were collected after 48 h and cytokines were measured by ELISA.
- Immunosuppressive effect of different doses of Caerulomycin A was monitored on naïve $CD4^+$ T cells, antigen reactive $CD4^+$ T cells, Th2 clone and Th1 hybridoma. The cells were incubated with γ-irradiated (3000 Rads) and antigen-pulsed splenocytes and various concentrations of Caerulomycin A (0.00625-0.1 μg/ml). The cultures were incubated at 37° C. and 7% $CO_2$. After 72 h, the cultures were pulsed with 0.5 μCi of [$^3$H]-thymidine and harvested 14 h later. Radioactivity incorporated was measured by liquid scintillation.
- Immunosuppressive effect of Caerulomycin A on MLR reaction. The MLR was performed using BALB/c splenocytes (responder cells) and γ-irradiated C57BL/6J splenocytes (stimulator cells) with various concentrations of Caerulomycin A (0.0125-1 μg/ml) and a positive control of Cyclosporin A (0.0125-10 μg/ml). After 4 days, the cultures were pulsed with 1 μCi of [$^3$H]-thymidine and harvested 16 h later and radioactivity incorporated was measured by liquid scintillation counting.
- In vivo immunosuppressive effect of Caerulomycin A on the proliferation of T cells. Ovalbumin was emulsified in Freund's complete adjuvant and injected (100 μg/100 μl) intraperitoneally in different groups (5 mice/group) of animals. Different groups of antigen-primed animals were daily injected with Caerulomycin A (25, 50, 75, 100 μg/100 μl/mice). After seven days, mice were sacrificed and splenocytes were isolated, pooled for in vitro proliferation.
- Caerulomycin A induces immunosuppression by up regulating CTLA-4 and inhibiting CD28 expression on T cells. CD28 and CTLA-4 expression was detected by flowcytometry on the surface of resting and ConA activated $CD4^+$ T cells. The splenocytes were activated with either antigen (OVA) or mitogen (ConA) and were incubated for different duration (24, 48, 72 and 96 h) with Caerulomycin A (0.0125-0.45 μg/ml). The cultures were harvested after 24, 48, 72 and 96 h and the expression of CD28 and CTLA-4 on $CD4^+$ T cells was evaluated by 3-color staining using PE (phycoerythrin) conjugated anti-CD4 Ab, FITC (fluorescein isothiocyanate) conjugated anti-CTLA-4 Ab and Cy (cy-chrome) conjugated anti-CD28 Ab.
- Similarly, expression of B7-1, B7-2 and I-$A^d$ was also monitored by flowcytometry on peritoneal macrophages as mentioned in No. 6.

The compound Caerulomycin of the general formula 1, derivatives and pharmaceutically acceptable salts thereof are effective as immunosuppressive agents.

Advantages:

The main advantages of the present invention are follows:—

(i) Since $CD4^+$ T cell plays a crucial role in the initiation and regulation of immune responses, inhibition of their activation provides a powerful approach for immunosuppressive therapy. This has been very well documented in the case of many other immunosuppressive drugs and their treatment for autoimmunity (Galvin et al. 1993, Thomson 1991, Crespo-Leiro 2003). Moreover, the role of $CD4^+$ T cells is very well documented in many autoimmune diseases (Abbas et al. 2004, Wraith et al. 2004). Since Caerulomycin A suppressed the proliferation and cytokines (IL-4 and IFN-γ) secretion by naïve and antigen specific effector CD4+ T cells, therefore it will be quite promising drug in autoimmune diseases. Further, Caerulomycin A significantly augmented CTLA-4 and subsequently down-regulated CD28 expression on T cells. We also noticed increased quantity of CD4+ T cells expressing CTLA-4 and decrease in the number of CD28 positive cells. Similar results were observed in the case of non-CD4+ T cells. There is a growing appreciation for the concept that lymphocyte responses are suppressed by CTLA-4 mediated inhibitory signals (Krummel et al. 1996, Leibson 2004).

(ii) Recognition of allogeneic MHC molecules is the main obstacle to organ transplant survival. Hence inhibition of allo-recognition can reduce the incidence and severity of chronic rejection and will provide long-lasting survival of the transplanted organs. We observed a dose dependent inhibition in the MLR by Caerulomycin A and it was 10 fold more potent than Cyclosporin A (CsA), which is a well-established immunosuppressive drug. We observed that Caerulomycin A also inhibited the expression of MHC molecules. Elevated levels of allogeneic MHC are the main obstacles to organ transplant survival. Hence decrease in the expression of MHC molecules will provide graft a better chance of acceptance. Thus, indicating that Caerulomycin A can be effectively utilized in transplantation. Further, Caerulomycin A has an advantage over CsA because of the high incidence of cancer reported in CsA consumption (Rovira et al. 2000).

REFERENCES

The following references cited in this document are hereby incorporated by reference in their entirety and for all purposes.

Abbas A K, Lohr J, Knoechel B, Nagabhushanam V. T cell tolerance and autoimmunity. Autoimmun Rev. 3:2004:471-475.

Agrewala J N, Vinay D S, Joshi A, Mishra G C. A 150-kDa molecule of macrophage membrane simulates interleukin-2 and interferon-gamma production and proliferation of ovalbumin-specific CD4+ T cells. Eur J Immunol. 24:1994:2092-7.

Agrewala J N, Suvas S, Verma R K, Mishra G C. Differential effect of anti-B7-1 and anti-M150 antibodies in restricting the delivery of costimulatory signals from B cells and macrophages. J Immunol. 160:1998:1067-77.

Chandran R R, Sankaran R, Divekar P V. Phytotoxic properites of caerulomycin and some of its derivatives. J Antibiot (Tokyo). 1968:243.

Chatterjee D K, Raether W, Iyer N, Ganguli B N. Caerulomycin, an antifungal antibiotic with marked in vitro and in vivo activity against Entamoeba histolytica. Z Parasitenkd. 1984; 70(5):569-73.

Chambers C A, Kuhns M S, Egen J G, Allison J P. CTLA4-mediated inhibition in regulation of T cell responses: mechanisms and manipulation in tumor immunotherapy. Annu Rev Immunol. 19:2001:565-594.

Chen W, Jin W, Wahl S M. Engagement of cytotoxic T lymphocyte-associated antigen 4 (CTLA-4) induces transforming growth factor beta (TGF-beta) production by CD4 (+) T cells. J Exp Med. 188:1998:1849-57.

Crespo-Leiro M G. Tacrolimus in heart transplantation. Transplant Proc. 35:2003:1981-3.

Divekar P V, Read G, Vining L C. Caerulomycin, a new antibiotic from Streptomyces caeruleus Baldacci. I. Structure. Can J Chem. 45:1967:1215-22.

Funk A, Divekar P V. Caerulomycin, a new antibiotic from Streptomyces caeruleus Baldacci. I. Production, isolation, assay, and biological properties. Can J Microbiol. 5:1959:317-21.

Freeman G J, Long A J, Iwai Y, Bourque K, Chernova T, Nishimura H, Fitz L J, Malenkovich N, Okazaki T, Byrne M C, Horton H F, Fouser L, Carter L, Ling V, Browman M R, Carreno B M, Collins M, Wood C R, Honjo T. Engagement of the PD-1 immunoinhibitory receptor by a novel B7 family member leads to negative regulation of lymphocyte activation. J Exp Med. 92:2000:1027-34.

Galvin F, Freeman G J, Razi-Wolf Z, Benacerraf B, Nadler L, Reiser H. Effects of cyclosporin A, FK 506, and mycalamide A on the activation of murine CD4+ T cells by the murine B7 antigen. Eur. J. Immunol. 23:1993: 283-6.

Greenwald R J, Boussiotis V A, Lorsbach R B, Abbas A K, Sharpe A H. CTLA-4 regulates induction of anergy in vivo. Immunity. 14:2001:145-55.

Greenwald R J, Freeman G J, Sharpe A H. The B7 family revisited. Annu Rev Immunol. 23:2005:515-548.

Krummel M F, Allison J P. CTLA-4 engagement inhibits IL-2 accumulation and cell cycle progression upon activation of resting T cells. J Exp Med. 183:1996: 2533-40.

Lanzavecchia A, Lezzi G, Viola A. From TCR engagement to T cell activation: a kinetic view of T cell behavior. Cell. 96:1999:14.

Lee K M, Chuang E, Griffin M, Khattri R, Hong D K, Zhang W, Straus D, Samelson L E, Thompson C B, Bluestone J A. Molecular basis of T cell inactivation by CTLA-4. Science 282:1998:2263-66.

Leibson P J. The regulation of lymphocyte activation by inhibitory receptors. Curr Opin Immunol. 16:2004:328-36.

Linsley P S, Brady W, Urnes M, Grosmaire L S, Damle N K, Ledbetter J A. CTLA-4 is a second receptor for the B cell activation antigen B7. J Exp Med. 174:1991:561-9.

Nishimura H, Okazaki T, Tanaka Y, Nakatani K, Hara M, Matsumori A, Sasayama S, Mizoguchi A, Hiai H, Minato N, Honjo T. Autoimmune dilated cardiomyopathy in PD-1 receptor-deficient mice. Science. 291:2001:319-22.

Prashar Y, Khanna A, Sehajpal P, Sharma V K, Suthanthiran M. Stimulation of transforming growth factor-beta 1 transcription by cyclosporine. FEBS Lett. 358:1995:109-12.

Rovira P, Mascarell L, Truffa-Bachi P. The impact of immunosuppressive drugs on the analysis of T cell activation. Curr Med Chem. 7:2000:673-92.

Salomon B, Lenschow D J, Rhee L, Ashourian N, Singh B, Sharpe A, Bluestone J A. B7/CD28 costimulation is essential for the Homeostasis of the CD4+CD25+ immunoregulatory T cells that control autoimmune diabetes. Immunity 12:2000:431-40.

Salomon B, Bluestone J A. Complexities of CD281B7: CTLA4 costimulatory pathways in autoimmunity and transplantation. Annu. Rev. Immunol. 19:2001:225-52.

Stamper C C, Zhang Y, Tobin J F, Erbe D V, lkemizu S, Davis S J, Stahl M L, Seehra J, Somers W S, Mosyak L. Crystal structure of the B7-1/CTLA-4 complex that inhibits human immune responses. Nature 410:2001:608-11.

Takahashi T, Tagami T, Yamazaki S, Uede T, Shimizu J, Sakaguchi N, Mak T W, Sakaguchi S. Immunologic Self-tolerance maintained by CD25 (+) regulatory T cells constitutively expressing cytotoxic T lymphocyte-associated antigen 4. J Exp Med. 192:2000:303-10.

Thomson A W. The immunosuppressive macrolides FK-506 and rapamycin. Immunol Lett. 29:1991:105-11.

Tivol E A, Borriello F, Schweitzer A N, Lynch W P, Bluestone J A, Sharpe A H. Loss of CTLA-4 leads to massive lymphoproliferation and fatal multiorgan tissue destruction, revealing a critical negative regulatory role of CTLA-4. Immunity 3:1995:541-47.

Tivol E A, Schweitzer A N, Sharpe A H. Costimulation and autoimmunity. Curr. Opin. Immunol. 8:1996:822-830.

van der Merwe P A, Bodian D L, Daenke S, Linsley P, Davis S J. CD80 (B7-1) binds both CD28 and CTLA-4 with a low affinity and very fast kinetics. J. Exp. Med. 185:1997: 393-404.

Wraith D C, Nicolson K S, Whitley N T. Regulatory CD4+ T cells and the control of autoimmune disease. Curr Opin Immunol. 16:2004:695-701.

We claim:

1. A method for inducing immunosupression comprising administering to a patient in need thereof a 3,6-disubstituted-4-methoxy-2,2'-bipyridine compound of the general formula 1, or a pharmaceutically acceptable salt thereof:

(formula 1)

wherein, X=—CH:NOR$_1$; —COOR$_1$; —CHO; —CH$_2$OR$_2$;
Y=H; OR$_3$;
R$_1$H; C$_1$ to C$_{16}$ normal or branched chain alkyl;
R$_2$=H; C$_1$ to C$_{16}$ normal or branched chain alkyl; C$_1$ to C$_{16}$ normal or branched chain acyl;
R$_3$=H; methyl; ethyl; isopropyl or isobutyl.

2. The method as claimed in claim 1, wherein the compound is (E)-4-methoxy-2,2'bipyridine-6-carbaldehyde oxime (Caerulomycin A) of the formula 2:

(formula 2)

3. The method as claimed in claim 1, wherein the compound is (E)-4-methoxy-2,2'bipyridine-6-carbaldehyde 0-methyl oxime of the formula 3:

(formula 3)

4. The method as claimed in claim 1, wherein the compound is administered at a dosage ranging from 1.25 to 5.0 mg/kg body weight.

5. The method as claimed in claim 1, wherein the compound is 10 times more effective in inhibiting the immune response than cyclosporinA.

6. The method as claimed in claim 1, wherein about 0.1 μg of the compound per ml of a diluent inhibits about 90% to 97% of the immune cells within 48 hours.

7. The method as claimed in claim 1, wherein the compound inhibits in vitro proliferation of T cells, B cells, Naive CD4$^+$ T cells, antigen specific effector CD4$^+$ T cells, Th1 cells and Th2 cells, or a mixed lymphocyte reaction.

8. The method as claimed in claim 1, wherein the compound inhibits in vitro secretion of cytokines.

9. The method of any one of claims 1 to 8, wherein the compound down-regulates the expression of activation marker CD28 and up-regulates the expression of inhibition marker CTLA-4 on T cells.

10. The method as claimed in claim 1, wherein the compound increases the expression of B7-1 and decreases the expression of B7-2 and MHC molecules on macrophages.

11. The method as claimed in claim 1, wherein the compound induces suppression of αβ T cells and γδ T cells, CD4$^+$ T cells and CD8$^+$ T cells, Th 1 cells and Th 2 cells; naïve T cells, effector T cells, memory T cells and regulatory T cells.

12. The method as claimed in claim 1, wherein the said compound induces suppression of B cells, mast cells, endothelial cells, NK cells, dendritic cells, monocytes, macrophage, epithelial cells, osteoblasts, eosinophils, basophils, granulocytes, platelets and megakaryocytes.

13. The method as claimed in claim 1, wherein the immunosuppression reduces a graft versus host reaction.

14. The method as claimed in claim 1, wherein the compound is isolated from *Actinoalloteichus spitiensis* [MTCC 6194].

15. The method as claimed in claim 1, wherein the compound is administered in a single dosage form daily for 3 days.

16. The method of claim 8, wherein the cytokine is interferon-γ or interleukin-4.

17. The method of claim 12, wherein the dendritic cells are myeloid cells, plasmacytoid dendritic cells, lymphoid dendritic cells or interstitial dendritic cells and macrophages are splenic macrophages, peritoneal macrophages, alveolar macrophages, Kuffer's cells, Langerhans cells, osteoclasts or glial cells.

18. The method of claim 1, wherein the immunosuppression reduces a graft rejection or helps in transplantation.

19. The method of claim 2, The method as claimed in claim 2, wherein the immunosuppression reduces a graft versus host reaction.

20. The method of claim 2, wherein the immunosuppression reduces a graft rejection or helps in transplantation.

* * * * *